United States Patent [19]

Broadhurst et al.

[11] Patent Number: 4,992,453
[45] Date of Patent: Feb. 12, 1991

[54] CERTAIN THIOIMIDATE AND AMIDINE INSECTICIDES

[75] Inventors: Michael D. Broadhurst, Novato; Thomas H. Cromartie, Albany, both of Calif.

[73] Assignee: ICI Americas Inc., Wilmington, Del.

[21] Appl. No.: 468,457

[22] Filed: Jan. 22, 1990

Related U.S. Application Data

[62] Division of Ser. No. 122,878, Nov. 17, 1987, Pat. No. 4,931,448.

[51] Int. Cl.$^5$ ............... C07D 213/74; C07C 251/16; A01N 43/40; A01N 33/06
[52] U.S. Cl. .................. 514/338; 514/347; 514/349; 514/450; 514/452; 514/464; 514/641; 546/270; 546/297; 549/362; 564/276
[58] Field of Search ............ 514/338, 347, 349, 450, 514/452, 464, 641; 549/362; 546/270, 297; 564/276

[56] References Cited

U.S. PATENT DOCUMENTS 4,427,699 1/1984 Lee ........................ 564/27

FOREIGN PATENT DOCUMENTS 239535 9/1987 European Pat. Off. ............ 546/291

OTHER PUBLICATIONS

Salbeck et al., Pesticide Science, vol. 13, pp. 647–652, (1982).
Tanaka et al., Agric. Biol. Chem., vol. 41, pp. 1953–1959 (1977).

Primary Examiner—Alan L. Rotman
Attorney, Agent, or Firm—Joel G. Ackerman

[57] ABSTRACT

Insecticidal compounds having the formula

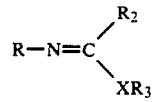

in which R is an optionally substituted aryl moiety; $R_2$ is an optionally substituted alkyl, cycloalkyl or alkenyl moiety, X is sulfur, amino or $C_1$–$C_4$ monoalkylamino; and $R_3$ is: (a) an optionally substituted 3-phenoxyphenalkyl, 3-phenoxypyridylalkyl or 3-(4-pyridyloxy)phenalkyl moiety; (b) pentafluorobenzyl; or (c) 2-methyl-3-phenylbenzyl.

12 Claims, No Drawings

CERTAIN THIOIMIDATE AND AMIDINE INSECTICIDES

This is a divisional, of application Ser. No. 122,878, filed Nov. 17, 1987, now U.S. Pat. No. 4,931,448.

BACKGROUND OF THE INVENTION

This invention relates to a series of novel imidate insecticides distinguished by the general formula $$R-N=C\begin{matrix}R_2\\XR_3\end{matrix} \quad (I)$$

in which
R is an optionally substituted aryl moiety; $R_2$ is an optionally substituted alkyl, cycloalkyl or alkenyl moiety, X is sulfur, amino or $C_1$-$C_4$ monoalkylamino and $R_3$ is (a) an optionally substituted 3-phenoxyphenalkyl, 3-phenoxypyridylalkyl or 3-(4-pyridyloxy)phenalkyl moiety; (b) pentafluorobenzyl; or (c) 2-methyl-3-phenylbenzyl.

More specifically, the compounds have the formula (II)

in which
$R_1$ is 4-halo; 4-methyl; 3,4-disubstitution in which the substituents are independently halo, methyl, trifluoromethyl, trifluoromethylthio, trifluoromethoxy; or a 3,4-alkylenedioxy group having from 1 to 4 carbon atoms, optionally substituted by up to 2 halogens;
$R_2$ is methyl; ethyl; n-propyl; $C_3$-$C_7$ branched alkyl; $C_1$-$C_6$ haloalkyl; or cyclopropyl, optionally substituted by up to 4 methyl groups or up to 2 halogens;
$R_3$ is (a)

in which:
m is 0 or 1;
A and B are independently N or —CH,
$R_4$ is hydrogen or halo;
$R_5$ is hydrogen, mono- or di-halo, $C_1$-$C_4$ alkyl, $C_1$-$C_4$ alkoxy, $C_1$-$C_4$ alkylthio, trifluoromethyl, cyano, or $C_1$-$C_4$ alkylsulfonyl; and
$R_6$ is hydrogen or methyl;
(b) pentafluorobenzyl; or
(c) 2-methyl,3-phenylbenzyl;
X is sulfur, amino or $C_1$-$C_4$ monoalkylamino; provided that:
(i) if $R_1$ is 4-chloro and $R_2$ is dichloromethyl, then X is not sulfur and $R_3$ is not pentafluorobenzyl;
(ii) if $R_1$ is 4-fluoro and $R_2$ is cyclopropyl, then X is not amino or monoalkylamino; and
(iii) $R_2$ is not, 1,3-dihalopropyl.

The compounds of this invention demonstrate activity in controlling various types of insects, primarily in controlling lepidoptera.

Another aspect of this invention is an insecticidal composition comprising an insecticidally effective amount of a compound of the invention formulated with an insecticidally suitable diluent or carrier.

Another aspect of this invention is a method for controlling insects by administration of insecticidally effective amounts of the compounds or compositions of this invention to the locus of the insect infestation.

The term "halo" includes chloro, bromo, iodo and fluoro. Of these, chloro is preferred. "Alkyl" refers to saturated acyclic hydrocarbyl groups (straight or branched chain) having the indicated number of carbon atoms. "Haloalkyl" refers to such groups substituted by one or more halogens, preferably chloro. "Alkylsulfonyl" refers to an alkyl group of the indicated number of carbon atoms, bonded to a sulfonyl (—$SO_2$) group. Preferred groups in this invention include methyl, ethyl, isopropyl, chloromethyl, dichloromethyl and methylsulfonyl.

Alkylenedioxy moieties include methylenedioxy (—O—$CH_2$—O—), 1,2-ethylenedioxy (—O—$C_2H_4$—O—), monohalomethylenedioxy $$-(O-\underset{Hal}{CH}-O-),$$

dihalomethylenedioxy $$(-O-\underset{\underset{Hal}{|}}{\overset{\overset{Hal}{|}}{C}}-O-),$$

1,1-ethylenedioxy $$(-O-\underset{\underset{CH_3}{|}}{CH}-O-),$$

and isopropylenedioxy —(O—C($CH_3$)$_2$—O—), wherein "Hal" represents a halogen atom.

Unsubstituted groups having the formula include 3-phenoxybenzyl, 3-phenoxy-(alpha-methyl)-benzyl, 3-phenoxyphenethyl, 3-phenoxypyridylmethyl and 4-pyridyloxybenzyl. Substituents include, for $R_4$: 4- and 6-mono-halo, particularly monofluoro; for $R_5$: 2-, 3- or 4-halo; 2,4- 3,4- or 3,5-dihalo; 4-trifluoromethyl; 4-cyano 4-methoxy; 4-methylthio; and 4-methylsulfonyl.

The term "amino" as used herein indicates the group —NH—.

Compounds of this invention may be prepared by reaction of an imidoyl chloride with a mercaptan, an alkali metal mercaptide, or an amine according to the reaction:

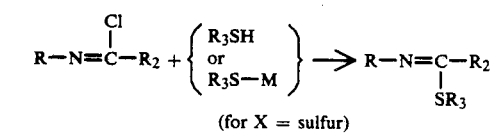

(for X = sulfur)

or

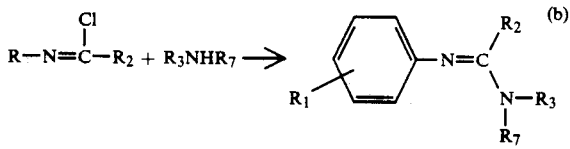

in which R, $R_2$, $R_3$ are as defined above, M is an alkali metal, preferably sodium or potassium, and $R_7$ is hydrogen or $C_1$–$C_4$ alkyl.

Reaction (a) or (b) is conducted in a temperature range of from about −40° C. to about 80° C., most preferably from about −10° to about 20° C., for a time which may range from about 10 minutes to about 20 hours. The reaction may be conducted in the presence of a solvent, for example, an aromatic hydrocarbon such as benzene, toluene, xylene or naphthalene, or an ether, such as diethyl ether, diisopropyl ether, diisoamyl ether, dibutyl ether, furan, 1,2-dimethoxyethane, or tetrahydrofuran (preferably tetrahydrofuran).

Alkali metal mercaptides $R_3S$-M may be produced by reaction of an appropriate mercaptan, such as 3-phenoxybenzyl mercaptan, with an alkali metal-containing base, for instance, an alkali metal hydride (e.g., potassium or preferably sodium hydride) in the presence of a solvent which may be an aromatic hydrocarbon such as benzene, toluene, xylene or naphthalene or an ether, such as diethyl ether, diisopropyl ether, diisoamyl ether, dibutyl ether, furan, 1,2-dimethoxyethane or tetrahydrofuran. In general, this reaction is conducted at reflux temperature under an inert atmosphere for a time which may range up to about 2 hours.

The imidoyl chloride may be prepared from a starting amine having the formula $RNH_2$ or amide having the formula

depending on availability. The amines are either generally available or may be prepared by procedures known in the art, for example, those described in "Compendium of Organic Synthetic Methods", Harrison et al. (Wiley-Interscience, N.Y., 1971).

The amides, if not available, may be produced by reaction of the amine with an appropriate acid chloride having the formula

The temperature of this reaction ranges from about −40° C. to about +80° C. Suitable solvents include hydrocarbon solvents such as toluene and chlorinated hydrocarbon solvents such as methylene chloride, chloroform, carbon tetrachloride, ethylene dichloride, tetrachloroethane and the like, preferably methylene chloride. This reaction is conducted in the presence of a base, preferably a tertiary amine. Suitable bases include triethylamine, quinoline, dimethylaniline, diethylaniline, and pyridine. Triethylamine is the preferred base. The resulting amide is recovered and purified by conventional means.

The imidoyl chloride may be prepared from the amide by reacting it with a chlorinating agent such as phosphorus pentachloride in an organic solvent such as that utilized in the amide production (preferably methylene chloride) or alternatively using phosphorus oxychloride as the solvent. The reaction is carried out under an inert atmosphere for a time which may range up to 10 hours, preferably from 1 to 4 hours, at a temperature of from about 0° C., to about 80° C.

Before the imidoyl chloride-containing product is passed to the final step, all substances, such as phosphorus oxychloride or hydrogen chloride, which can react with the mercaptan or mercaptide in the final step, should be removed. This can generally be accomplished by evaporation or distillation.

If a mercaptan is used in reaction (a), the process is carried out in the presence of a suitable base. The base utilized is a tertiary amine such as that employed for production of the amide from the amine and is preferably triethylamine. This reaction is conducted in the presence of a suitable solvent such as that utilized in the reaction of the alkali metal mercaptide with the imidoyl chloride, and is preferably tetrahydrofuran. The reaction between the mercaptan and the imidoyl chloride can be exothermic; consequently the addition of imidoyl chloride should be carefully controlled. This process carried out at room temperature under reflux for a time of between about 30 and about 60 minutes. The product may be recovered by conventional techniques.

Mercaptans of the formula $R_3SH$ are described in German Appln. No. 2,944,849. 3-Phenoxybenzylamine is described in European Application No. 6155.

Compounds in which X is sulfur may also be prepared by alkylation of a thioamide according to the equation:

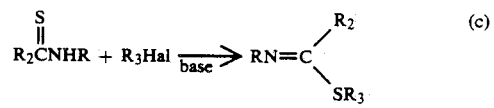

in which R, $R_2$ and $R_3$ are as defined above and Hal stands for halogen, preferably chloro.

The thioamides, if not readily available, may be produced by reaction of the corresponding amine and Lawesson's Reagent. Reaction (c) is generally conducted at a temperature of from about −20° to about 80° C., for a time of from about 1 to about 20 hours, in the presence of a solvent, for instance an aromatic hydrocarbon such as benzene, toluene, xylene or naphthalene, or an ether such as diethyl, diisopropyl, diisoamyl or dibutyl ether, furan, 1,2-dimethoxyethane or tetrahydrofuran and an appropriate base such as an alkali metal hydride.

The following represent examples of the preparation of compounds of this invention.

EXAMPLE 1

This example illustrates the general procedure for the preparation of insecticidal amidines (X is amino or alkylamino).

Preparation of
N-(4-Chlorophenyl)-N-(3-phenoxybenzyl)isobutyramidine (Compound 2)

A. Step 1: Preparation of 4-Chloroisobutyrylanilide

To a stirred solution of 10 grams (g) (0.078 mol) 4-chloroaniline and triethylamine (11.2 ml, 0.08 mol) in 100 ml of dichloromethane was added 7.8 ml (0.075 mol) of isobutyryl chloride dropwise with cooling in an ice bath. Following the addition, the ice bath was removed and when the reaction mixture reached room temperature, 100 ml of water was added. The layers were separated and the organic layer was dried over anhydrous sodium sulfate. Rotary evaporation provided the desired product.

Step 2: Preparation of N-(1-Chloro-2-methylpropylidine)-4-chloroaniline

To a stirred solution of 4-chloroisobutyrylanilide (2.0 g, 0.010 mol) in 50 ml of dichloromethane under an argon atmosphere was added phosphorus pentachloride ($PCl_5$) (2.1 g, 0.010 mol). After 2 hours, the resulting solution was transferred to a rotary evaporator. The solvent was removed at 20 mm Hg and the residue was evaporated at 40° under a vacuum of less than 1 mm Hg. The resultant N-(1-chloro-2-methylpropylidine)-4-chloroaniline, a viscous oil, was immediately carried on to Step 3.

Step 3: Preparation of Amidine 1.8 g (0.0083 mol) of N-(1-chloro-2-methylpropylidine)-4-chloroaniline, 2.0 g (0.011 mol) of 3-phenoxybenzylamine (prepared from 3-phenoxybenzonitrile according to a method described in EPO Application No. 6,155), 2.0 g (2.8 ml, 0.02 mol) of triethylamine and 10 ml of tetrahydrofuran were mixed in a flask equipped with a magnetic stirrer, thermometer and a dropping funnel, under argon, overnight. The crude product mixture was filtered and the residue was washed with tetrahydrofuran. Rotary evaporation gave 3.8 g of a yellow oil, which by was identified by spectroscopic analyses as N-(4-chlorophenyl)-N-(3-phenoxybenzyl)isobutyrylamidine.

EXAMPLE 2

This example illustrates the general procedure for the preparation of insecticidal thioimidates (X is sulfur).

Preparation of
N-(4-Chlorophenyl)-S-(3-phenoxybenzyl)isobutyryliminothioate (Compound 3)

2.1 g (0.010 mol) of N-(1-chloro-2-methylpropylidine)-4-chloroaniline, prepared as in Example 1, was mixed with 1.11 g (0.011 mol) of triethylamine and 50 ml of 1,2-dichloroethane in a 100 ml, 3-necked, round-bottomed flask, under argon. It was then cooled in an ice bath below 10° C. When the temperature reached 3° C., 2.16 g (0.010 mol) of 3-phenoxybenzyl mercaptan was added within 2 minutes. When the addition was complete, the ice bath was removed and the mixture was stirred at room temperature overnight. The reaction mixture was then washed twice with 25 ml of water and once with 25 ml of saturated sodium chloride solution. The organic layer was separated, dried over magnesium sulfate, filtered, and concentrated on a rotary evaporator at 26° C., at 1 mm Hg. Yield, 4.8 g of a waxy oil. The structure was confirmed by spectroscopic analyses.

The following Table I depicts representative compounds of the invention.

TABLE 1

$$\text{R}_1\text{-C}_6\text{H}_4\text{-N=C}(R_2)(XR_3)$$

| Cmpd. No. | X | $R_1$ | $R_2$ | $R_3$ | Physical Constant |
|---|---|---|---|---|---|
| 1 | NH | 4-Cl | $CHCl_2$ | 3-phenoxybenzyl | oil |
| 2 | NH | 4-Cl | isopropyl | 3-phenoxybenzyl | oil |
| 3 | S | 4-Cl | isopropyl | 3-phenoxybenzyl | oil |
| 4 | NH | 4-$CH_3$ | $CHCl_2$ | 3-phenoxybenzyl | oil |
| 5 | $NCH_3$ | 4-$CH_3$ | $CHCl_2$ | 3-phenoxybenzyl | oil |
| 6 | $NCH_3$ | 4-Cl | $CHCl_2$ | 3-phenoxybenzyl | oil |
| 7 | S | 3-Cl, 4-F | isopropyl | 3-phenoxybenzyl | oil |
| 8 | NH | 3-Cl, 4-F | isopropyl | 3-phenoxybenzyl | oil |
| 9 | NH | 3,4-(-O-$CH_2$-O-) | isopropyl | 3-phenoxybenzyl | oil |
| 10 | S | 3,4-(-O-$CH_2$-O-) | isopropyl | 3-phenoxybenzyl | oil |
| 11 | $NCH_3$ | 4-Cl | isopropyl | 3-phenoxybenzyl | oil |

Insecticidal Evaluation Tests

The compounds in Table 1 were tested for insecticidal activity using the following testing procedures. $LD_{50}$ values, based on the results of these tests and calculated according to dosage-mortality curves, are expressed in Table 2.

Housefly [*Musca domestica*]

The test compound was diluted in acetone and aliquots pipetted onto the bottom of aluminum dishes. To ensure even spreading of the chemical on the bottom of the dishes, 1 ml of acetone containing 0.01% peanut oil was also added to each dish. After all solvents had evaporated, the dishes were placed in circular cardboard cages containing 25 female houseflies, 1-2 days old. The cages were covered on the bottom with cellophane and on the top with tulle netting, and each contained a sugar-water saturated cotton plug for maintenance of the flies. Mortality was recorded after 48 hours. Test levels ranged from 100 µg/25 female houseflies downward. The LD-50 value is expressed below in Table II under the heading "HF", in terms of µg of the test compound per 25 female flies.

Black Bean Aphid [*Aphis fabae* (Scop.)]

Nasturtium plantes (Tropaeolum sp.) approximately 5 cm tall, were transplanted into sandy loam soil in small cups and infested with 25-50 black bean aphids of mixed ages. Twenty-four hours later they were sprayed to the point of runoff with 50-50 acetone-water solutions of the test compound. Treated plants were held in the greenhouse and mortality was recorded after 48 hours. Test concentrations ranged from 0.05% downward. The LD-50 value is expressed below in Table II under the heading "BA" in terms of percent of the test compound in the sprayed solution.

Tobacco Budworm [*Heliothis virescens* (Fabricius)]

(a) Contact: Test compounds were diluted in a 50-50 acetone-water solution. Cotton (*Gossypium sp.*) cotyledons were immersed in the test solutions for 2-3 seconds and placed on a wire screen to dry. The dried leaves were placed in petri dishes containing a moistened piece of filter paper and infested with 5 second-instar tobacco budworm larvae. The dishes were placed in a high humidity chamber for 5 days, and percent mortality of the larvae recorded. Test concentrations ranged from 01.1% downward. The LD-50 values are expressed below in Table II under the heading "TBW-C" in terms of percent of the test compound in the solution.

(b). Eggs: Paper towel patches of 2-day old eggs of the tobacco budworm were dipped in acetone solutions of the test compound and placed in petri dishes containing a portion of larval rearing medium. Treated eggs were maintained at 78° F. and mortality was recorded after all control eggs had hatched and the young larvae were feeding on the media. Test concentrations ranged from 0.1% downward. The LD-50 value is expressed below in Table II under the heading "TBW-E" in terms of percent of the test compound in the solution.

Cabbage Looper [*Trichoplusia ni* (Hubner)]

The test compound was diluted in a 50-50 acetone-water solution. Cotyledons of hyzini squash (*Calabacita abobrinha*), approximately 1×1.5 inches, were immersed in the test solutions for 2-3 seconds and placed on a wire screen to dry. The dried leaves were placed in petri dishes containing a moistened piece of filter paper and infested with 5 second-instar cabbage looper larvae. The dishes were placed in a high humidity chamber. Mortality of the larvae was recorded 5 days later. Test concentrations ranged from 0.1% downward. The LD-50 value is expressed below in Table II under the heading "CL" in terms of percent of the test compound in solution.

Beet Armyworm (*Spodoptera exigua*)

Test compounds were diluted in a 50-50 acetone-water solution. Young leaves of sugar beets (*Beta vulgaris*) were immersed in the test solutions for 2-3 seconds and placed on a wire screen to dry. The dried leaves were placed in petri dishes containing a moistened filter paper and infested with five second-instar beet armyworm larvae. The dishes were placed in a high humidity chamber. Mortality of the larvae was recorded five days later. Test concentrations ranged from 0.1% downward. The LD-50 values are expressed below in Table II under the heading "BAW" in terms of percent of the test compound in solution.

Western Spotted Cucumber Beetle Larvae [*Diabrotica undecimpunctata undecimpunctata* (Mannherheim)]

Ten grams of moist potting soil was placed in a plastic cup. The test compound was dissolved in acetone. A 0.05 ml aliquot of the test sample, diluted to the desired concentration, was added to the soil. The cup was capped and the soil was mixed on a vortex mixer for approximately 15 seconds. An indentation was made on the surface of the soil and approximately 50 Diabrotica eggs were added. The eggs were covered with soil and maintained at room temperature (approximately 70° F. or 21° C.). Four days later a section of Romaine lettuce (*Latuca sativa*) leaf was placed in the treated cups. One week later the cups were examined for live larvae. Test concentrations ranged from 25 ppm downward. The LD-50 value is expressed below in Table II under the heading "Diabrotica" in terms of ppm of the test compound in the soil.

Acaricidal Evaluation Test

The two-spotted mite (2SM) [*Tetranychus urticae* (Koch)] was employed in tests for miticides. The test procedure was as follows:

Pinto bean plants (Phaseolus sp.) approximately 10 cm tall, were transplanted into sandy loam soil in small cups and thoroughly infested with two-spotted mites of mixed ages and sexes. Twenty-four hours later the infested plants were inverted and dipped for 2-3 seconds in 50-50 acetone-water solutions of the test compound. Treated plants were held in the greenhouse, and 7 days later mortality was determined for both adult mites and the nymphs hatching from eggs which were on the plants at the time of treatment. Test concentrations ranged from 0.05% downward. The LD-50 value is expressed below in Table II under the headings "2SM-A" (i.e., adults) and "2SM-E" (i.e. eggs) in terms of percent concentration of the test compound in the solution.

The results of these tests are shown in Table II.

TABLE 2

| Cmpd. No. | HF µg | BA % | 2-SM A, % | 2-SM E, % | TBW C % | TBW E, % | BAW | CL, % | Diabrotica, ppm (soil) |
|---|---|---|---|---|---|---|---|---|---|
| | | | | | (LD$_{50}$) | | | | |
| 1 | <10 | 0.01 | >0.05 | >0.05 | 0.007 | 0.035 | 0.007 | 0.02 | >25 |

TABLE 2-continued

| Cmpd. No. | HF μg | BA % | 2-SM A, % | 2-SM E, % | TBW (LD$_{50}$) C % | TBW E, % | BAW | CL, % | Diabrotica, ppm (soil) |
|---|---|---|---|---|---|---|---|---|---|
| 2 | 47 | >0.05 | >0.05 | >0.05 | >0.1 | >0.1 | >0.1 | — | >25 |
| 3 | >100 | 0.05 | >0.05 | >0.05 | 0.03 | >0.05 | 0.05 | 0.01 | — |
| 4 | 8 | 0.01 | >0.05 | >0.05 | 0.02 | 0.1 | 0.045 | 0.02 | >25 |
| 5 | >100 | >0.05 | >0.05 | >0.05 | >0.1 | >0.1 | >0.1 | 0.04 | >25 |
| 6 | >100 | 0.006 | — | — | — | >0.1 | 0.05 | 0.009 | >25 |
| 7 | >100 | — | >0.05 | >0.05 | — | >0.1 | — | 0.0045 | >25 |
| 8 | 80 | — | >0.05 | >0.05 | — | >0.1 | — | 0.005 | >25 |
| 9 | >100 | — | >0.05 | >0.05 | — | >0.1 | — | 0.05 | >25 |
| 10 | >100 | — | >0.05 | >0.05 | — | >0.1 | — | 0.0023 | >25 |
| 11 | >100 | 0.05 | >0.05 | >0.05 | — | >0.1 | — | 0.04 | >25 |

Key:
C = Contact Test
E = Test on eggs
A = Test on adults

The insecticidal activity and therefore the inclusion of a compound within the class of compounds of this invention as defined by formula (I), may be determined by evaluating such a compound using one or more of the above-described procedures. If a test compound demonstrates activity against one or more of the insects mentioned, by virtue of having an LD$_{50}$ at the initial evaluation level, it is considered "insecticidal" for the purposes of this invention.

In practice, a pure compound I (active compound) can be used as an insecticide. However, in general, the compounds are first formulated with one or more inert (i.e. non-chemically reactive, plant compatible or herbicidally inert) carriers or diluents suitable for insecticidal use, before being applied.

The compositions or formulations, including a compound (I) as described herein, may take any one of a number of solid or liquid forms. Examples of solid forms are dusts, granules, tablets, powders and the like. Examples of liquid forms are emulsions, solutions, suspensions, flowables, emulsifiable concentrates and pastes. Such compositions may contain, in addition to the active compound or compounds, various carriers or diluents; surface-active agents (wetting agents, dispersing agents and/or emulsifying agents); solvents (water, or organic solvents such as aromatic solvents or chlorinated aliphatic solvents); adhesives; thickeners; binders; anti-foaming agents; and other substances as mentioned herein. Solid carriers or diluents included in such compositions or formulations may include, for example, ground natural minerals such as kaolins, alumina, calcined diatomaceous earth, calcium carbonate, silica, kieselguhr, clays, etc.; ground synthetic minerals such as various silicates and alumino-silicates and ground vegetable products such as bark, cornmeal, sawdust, cellulose powder and the like. Compositions containing sorptive clays will usually also contain a stabilizer, such as a glycol, to prevent or minimize degradation of the active ingredient.

To manufacture solid compositions, the active compounds are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of akali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents may also added.

Flowables are prepared by mixing an active compound with one or more dispersing agents and/or solid additives, and a liquid (which may be water or an organic solvent) in which the active compound is relatively insoluble, and grinding the mixture.

Both liquid and solid compositions may be in microcapsule or encapsulated form, to permit release of the enclosed active compound at a controlled rate over a period of time. Liquid compositions of this type contain encapsulated droplets of approximately 1-50 microns in diameter, including the active compound and optionally a solvent. The encapsulating material is an inert porous membrane of a polymeric material.

Solid encapsulated compositions generally take the form of granules, in which the liquid containing the active component is trapped in the pores of the granular support by a porous polymeric membrane through which the active ingredient may migrate at a controlled rate, or which membrane breaks down at a controlled rate to permit escape of the active ingredient.

Typical encapsulating materials include natural and synthetic rubbers, cellulosic materials, styrene-butadiene copolymers, polyacrylonitriles, polyacrylates, polyamides, polyisocyanates, polyurethanes, mixed copolymers of the foregoing and starch xanthates.

It is possible to use highly concentrated liquid compositions containing up to about 95% by weight of the active compound, or even the 100% active compound alone, when applying the compound in the form of a finely divided liquid by use of various atomizing equipment, for example by airplane spraying techniques. For other purposes, however, the various types of compositions which can be utilized for these compounds will contain varying amounts of the compound according to the type of composition and the intended use.

In general, insecticidal compositions may contain from 5 to 95% of the active compound, more preferably from 10 to 85%. Some typical compositions will contain an active compound as follows: wettable powders: 25 to 80% active compound; oil suspensions, emulsions, solutions, flowables, and emulsifiable concentrates: 5 to 85% active compound; aqueous suspensions: 20 to 50% active compound; dusts and powders: 5 to 20% active compound; granules and pellets: 5 to 20% active compound.

In addition to the active compound and the various agents utilized in preparing compositions and formulations mentioned, such compositions may also contain one or more other active compounds of the type mentioned herein as well as other active pesticidal agents, such as herbicides, fungicides, insecticides, acaricides, nematocides, bactericides, and plant growth regulators. Such compounds may also contain soil disinfectants or fumigants and may further contain fertilizers, thus making it possible to provide multi-purpose compositions containing one or more of the active compounds described herein as well as, optionally, other pesticides and also fertilizers, all intended and formulated for use at the same locus.

Control of insect pests is accomplished by applying a composition containing an insecticidally effective amount of an active compound as described herein to the insect, to a locus at which insecticidal control is desired, or to food sources (including seeds) on which the insects feed. For use in the last mentioned manner it is preferable to utilize a compound which is not volatile. Thus, control may be achieved by direct application of the active compounds to the insects and indirectly by application of the compounds to a locus to be protected (such as crop lands, grass ranges and forests), to a source of food for insects or to other insect habitats (for example, breeding or swarming areas. The rates of application of the active compound, and the concentration applied, will vary according to whether the compound or composition is being directly applied to the insect or indirectly, to a locus, food or habitat. In the latter case the rate of the application, depending on the nature of the insect or insects to be controlled, and the plant environment, will generally vary from about 0.01 to about 100 pounds per acre (about 0.011 to about 111 kg/ha).

It should be noted that the active compound need not be insecticidally active per se to effect insect control. The purposes of this invention are fully served if such compounds are rendered active by external influences, such as light or heat, or by some physiological action which occurs when the compound is ingested into the body of the insect.

Compositions containing one or more of the active compounds described, in an insecticidally effective amount, may be applied to the plant, locus or insect habitat in any conventional manner.

When used in connection with crop or other plant protection, application may be made in a preventive (i.e. before infestation) or eradicative manner (i.e., after infestation). Thus, powders and various liquid compositions containing the active compound can be applied by the use of power dusters, boom and hand sprayers and spray dusters, or applied from airplanes as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions including active compounds may additionally be used to protect plant seeds from being attacked by soil-borne insect pests after planting and during germination, by applying the composition to the seeds as a seed dressing. This is performed generally by mixing the seeds with an active composition in either liquid or solid form (preferably liquid) in a suitable mixing apparatus. Liquid compositions for this purpose may contain an adhesive or sticking agent, such as methyl cellulose, ethyl cellulose, etc., to assist the composition in adhering to the seed. If a solid composition is utilized for the purpose, an adhesive agent may be sprayed on the seeds during or after mixing.

For use as a soil insecticide, the active compound, or compositions containing it, may be mixed with the soil in any conventional manner, before, during or after planting of the plant seeds. Liquid compositions may be applied by spraying onto the surface or by incorporation in irrigation or sprayed water. Solid or liquid compositions containing an active compound may be incorporated into the soil prior to or during planting by discing, plowing or other mixing operations, or after planting as a side dressing, in order to locate the active ingredient below the surface of the soil so as to be most effective in controlling undesirable larvae.

Some examples of compositions containing the active compounds of this invention are:

| Composition A: Granular Solid | |
| --- | --- |
| Component | Weight % |
| Active compound | 10 |
| attapulgite clay granules | 85 |
| triethylene glycol | 5 |
| Total | 100% |

| Composition B: Wettable Powder | |
| --- | --- |
| Component | Weight % |
| Active compound | 80 |
| wetting agent (sodium dialkyl-naphthalene sulfonate) | 1 |
| dispersing agent (sodium lignosulfonate) | 4 |
| diluent (aluminum magnesium silicate) | 15 |
| Total | 100% |

| Composition C: Dilute Solution | |
| --- | --- |
| Component | Weight % |
| Active compound | 5 |
| solvent (xylene) | 95 |
| Total | 100% |

| Composition D: Emulsifiable Concentrate | |
| --- | --- |
| Component | Weight % |
| Active compound | 50 |
| Emulsifier (blend of metal sulfonates and polyoxy-ethylene ethers) | 10 |
| solvent (xylene) | 40 |
| Total | 100% |

| Composition E: Concentrated Solution | |
| --- | --- |
| Component | Weight % |
| Active compound | 90 |
| solvent (xylene) | 10 |
| Total | 100% |

What is claimed is:

1. A compound having the formula

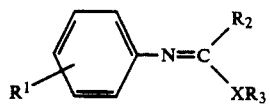

in which:

$R_1$ is 4-halo; 4-methyl; 3,4-disubstituted in which the substituents are independently halo, methyl, trifluoromethyl, trifluoromethylthio, trifluoromethoxy; or a 3,4-alkylenedioxy group having from 1 to 4 carbon atoms, optionally substituted by up to 2 halogens;

$R_2$ is methyl; ethyl; n-propyl; $C_3$-$C_7$ branched alkyl; $C_1$-$C_6$ haloalkyl; or cyclopropyl, optionally substituted by up to 4 methyl groups or up to 2 halogens;

$R_3$ is

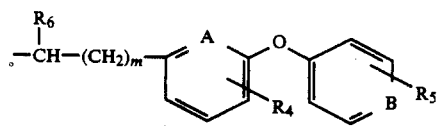

(a)

in which:

m is 0 or 1;

A is N or —CH; B is CH;

$R_4$ is hydrogen or halo;

$R_5$ is hydrogen, mono- or di-halo, $C_1$-$C_4$ alkyl, $C_1$-$C_4$ alkoxy, trifluoromethyl, cyano, $C_1$-$C_4$ alkylthio, or $C_1$-$C_4$ alkylsulfonyl; and $R_6$ is hydrogen or methyl;

(b) pentafluorobenzyl; or (c) 2-methyl,3-phenylbenzyl; provided that:

(i) if $R_1$ is 4-fluoro then $R_2$ is not cyclopropyl; and (ii) $R_2$ is not 1,3-dihalopropyl and X is amino or mono-($C_1$-$C_4$)-alkylamino.

2. A compound according to claim 1 in which $R_2$ is isopropyl.

3. A compound according to claim 1 in which $R_2$ is dichlorometlyl.

4. A compound according to claim 1 in which $R_1$ is a 3,4-disubstitution.

5. A compound according to claim 1 in which $R_1$ is a 3,4-alkylenedioxy group.

6. A compound according to claim 1 in which $R_3$ is 3-phenoxybenzyl.

7. A compound according to claim 1 in which X is amino.

8. A compound according to claim 1 in which X is mono-($C_1$-$C_4$)-alkylamino.

9. A compound according to claim 1 in which $R_1$ is 4-halo, 4-methyl, 3,4-dihalo, or a 3,4-alkylenedioxy group; $R_2$ is methyl, ethyl, n-propyl, isopropyl, or $C_1$-$C_6$ haloalkyl; $R_3$ is

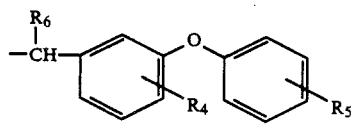

and X is —NH—, or —N(CH$_3$)—.

10. A compound according to claim 9 in which $R_1$ is a 3,4-dihalo substitution.

11. A method for controlling insects, comprising applying to the insect, to the locus of an insect, or to a locus at which insecticidal control is desired, an insecticidally effective amount of a compound according to claim 1.

12. An insecticidal composition comprising:

(a) an insecticidally effective amount of a compound according to claim 1; and (b) an insecticidally suitable inert diluent or carrier.

* * * * *

UNITED STATES PATENT AND TRADEMARK OFFICE
CERTIFICATE OF CORRECTION

PATENT NO. : 4,992,453

DATED : February 12, 1991

INVENTOR(S) : Michael D. Broadhurst and Thomas H. Cromartie

It is certified that error appears in the above-identified patent and that said Letters Patent is hereby corrected as shown below:

In Column 14, line 4, insert a semicolon after "1,3-dihalopropyl".

Signed and Sealed this

Nineteenth Day of April, 1994

Attest:

BRUCE LEHMAN

*Attesting Officer*     *Commissioner of Patents and Trademarks*